(12) United States Patent
Paufique

(10) Patent No.: US 8,277,850 B2
(45) Date of Patent: Oct. 2, 2012

(54) **USE OF AN ACTIVE INGREDIENT THAT IS OBTAINED FROM *CYPERUS ESCULENTUS* FOR ITS ANTI-AGING CUTANEOUS ACTION**

(75) Inventor: Jean Paufique, Objat (FR)

(73) Assignee: Societe Industrielle Limousine d'Application Biologique, Objat (FR)

( * ) Notice: Subject to any disclaimer, the term of this patent is extended or adjusted under 35 U.S.C. 154(b) by 190 days.

(21) Appl. No.: 12/863,596

(22) PCT Filed: Jan. 28, 2009

(86) PCT No.: PCT/FR2009/050128
§ 371 (c)(1),
(2), (4) Date: Jul. 20, 2010

(87) PCT Pub. No.: WO2009/095615
PCT Pub. Date: Aug. 6, 2009

(65) Prior Publication Data
US 2010/0291250 A1    Nov. 18, 2010

(30) Foreign Application Priority Data

Jan. 28, 2008   (FR) ...................................... 08 50502

(51) Int. Cl.
*A01N 65/00*   (2009.01)
(52) U.S. Cl. ...................................................... 424/725

(58) Field of Classification Search .................. None
See application file for complete search history.

(56) References Cited

U.S. PATENT DOCUMENTS 5,476,651 A   12/1995   Meybeck et al.

FOREIGN PATENT DOCUMENTS

WO   9220322 A1   11/1992

OTHER PUBLICATIONS

Parker Mary L et al."Esterified phenolics of the cell walls of Chufa (*Cyperus esculentus* L.) tubers and their role in texture", Journal of Agricultural and Food Chemistry, Dec. 2000, pp. 6284-6291, vol. 48, NR. 12, XP009105009.
International Search Report, Dated Jul. 31, 2009, in Application No. PCT/FR2009/050128.

*Primary Examiner* — Michael Meller
(74) *Attorney, Agent, or Firm* — Young & Thompson

(57) ABSTRACT

A method of treating cutaneous aging using of at least one active ingredient obtained from *Cyperus esculentus* in a cosmetic and/or dermopharmaceutical composition that is designed to combat cutaneous aging, preferably by working on the specific markers of the dermis. Cosmetic and/or dermopharmaceutical compositions that include an active ingredient that is obtained from *Cyperus esculentus*, an active ingredient that is obtained from *Cyperus esculentus*, and its production process.

1 Claim, No Drawings

USE OF AN ACTIVE INGREDIENT THAT IS OBTAINED FROM *CYPERUS ESCULENTUS* FOR ITS ANTI-AGING CUTANEOUS ACTION

This invention relates to the cosmetic use of an active ingredient that is obtained from *Cyperus esculentus* for combating cutaneous aging, preferably by working on specific markers of the dermis.

The invention also relates to an active ingredient that is obtained from *Cyperus esculentus*, to its production process, as well as to anti-aging compositions that comprise at least one active ingredient that is obtained from *Cyperus esculentus*.

The dermis is considered and recognized as the primary target of cosmetic active ingredients for combating cutaneous aging.

The dermis comprises a diversity of matrix molecules that are organized in a very dynamic structure that determines the biomechanical properties of the tissue and that plays an essential role during events linked to cell life. This macromolecular combination composes two dermal compartments that are separated by a vascular plexus: the papillary dermis or dermal papillae, and the reticular dermis.

The papillary dermis is a critical zone of the cutaneous tissue because of its key role in cohesion and in biomechanical properties of the skin, but also because it is the first target of intrinsic dermal aging.

The objective of this invention is to propose cosmetic products that can effectively combat cutaneous aging to assist in rejuvenating and revitalizing the skin by considering the aspects of aging of the skin on the various cutaneous layers, preferably by working on the specific markers of the papillary dermis.

To respond to this, the purpose of this invention is the use of an active ingredient that is obtained from *Cyperus esculentus* for the preparation of a cosmetic composition and/or a dermopharmaceutical composition that is designed to combat cutaneous aging.

The papillary dermis, located under the epidermal ridges, takes its name from its surface of papillae that form projections.

It consists of a loose connective tissue that contains heterotypical fine fibrillae that consist of collagen I and collagen of types III and V, which, contrary to those of the reticular dermis, are not very organized. These matrix collagens are involved in the matrix architecture, the resistance, the cohesion, and the flexibility of the skin.

The papillary dermis also contains oxytalan fibers or microfibrillae that consist primarily of fibrillins, large glycoproteins. These microfibrillae form a perpendicular network that is anchored in the basal membrane of the dermo-epidermal junction (DEJ). The microfibrillar network of the papillary dermis ensures the elastic properties of the skin and also creates a buffer zone endowed with a powerful "shock absorber" role of the DEJ in the case of great mechanical stresses.

A study conducted by the applicant showed that the synthesis of the fibrillin-1 by senescent papillary fibroblasts is significantly reduced relative to the normal control papillary fibroblasts.

This is why one objective of this invention is in particular to work on the synthesis of fibrillin-1 so as to restore the functional organization of the microfibrillar network of oxytalan of the papillary dermis.

Contrary to the reticular dermis, the papillary dermis also contains non-fibrillar collagens that are specific to it, the collagens of types XII and XVI, which contribute to the matrix scaffolding of this region.

Collagen XVI has a complex structure and is located only at the surface zone of the papillary dermis. It is associated exclusively with oxytalan fibers by interacting with fibrillin-1. It thus ensures the anchoring of oxytalan fibers to the basal membrane of the DEJ.

The study conducted by the applicant showed, however, that the expression of collagen XVI is significantly reduced on the senescent papillary fibroblasts compared to the normal papillary fibroblasts.

Another objective of this invention is therefore to work on the synthesis of the specific collagen XVI of the papillary dermis and thus to work on the flexibility and the functional organization of the microfibrillar network of oxytalan of the papillary dermis.

The expression of collagen XII is restricted to the papillary dermis. By linking the fibrillae of collagen I to the other matrix compounds, collagen XII regulates the biomechanical properties of the cutaneous tissue: deformability and contraction of the collagen fibers by promoting the sliding of fibers relative to one another.

One study conducted by the applicant showed, however, that the expression of collagen XII is significantly reduced on the senescent papillary fibroblasts compared to the normal papillary fibroblasts.

Also, this invention also proposes to work on the synthesis of the specific collagen XII of the papillary dermis with a view to working on the deformability of the papillary dermis.

Furthermore, it is known that the expression of collagen I is significantly reduced on the senescent papillary fibroblasts in comparison to the normal papillary fibroblasts.

Also, this invention proposes to work on the synthesis of collagen I, with a view to having an effect on the matrix architecture and the resistance of the papillary dermis.

In addition, the three-dimensional arrangement of the collagen fibers is facilitated by the presence of matrix molecules such as the proteoglycans, but also collagen VI. The special feature of collagen VI is its multiplicity of actions. It is actually linked to a large number of cells via integrin-type receptors as well as to multiple matrix molecules (collagen IV, fibronectins, biglycan, MAGP-1).

The expression of collagen VI is significantly reduced on the senescent papillary fibroblasts.

This is why this invention proposes to work on the synthesis of collagen VI with a view to improving the cohesion and the flexibility of the papillary dermis. To meet its objective, the purpose of this invention is therefore the use of an active ingredient that is obtained from *Cyperus esculentus*.

*Cyperus esculentus* is a hardy sedge of the Cyperaceae family, which measures from 30 to 40 cm in height and which has spindly rootstocks that thicken into egg-shaped or subglobular tubers of the size of a hazelnut, linear leaves, shorter than the stem with a width of 5 mm, pale green, smooth-faced with 3 to 5 bracts, and green or yellowish spikelets, 8 to 15 mm in length with glumes with 3 to 4 striae on each side. It is a plant that is widely used in the world, in particular in Africa, on the Mediterranean border, and in North America.

The *Cyperus esculentus* or rushnut is primarily known for its culinary properties. Its tubers with an almond taste can be consumed raw or dried, and the milk that is extracted from these tubers is used in the preparation of culinary specialties, in particular in Spain. In addition, it was used in the past by Egyptians and Native Americans as a base food that can substitute for cereal grains and in certain countries of Africa as an important nutrient element.

It is also known that the oil that is extracted from the *Cyperus esculentus* tubers can be used as an ingredient for the production of soaps and lubricants, or else as perfume as in Burkina Faso.

*Cyperus esculentus* also has medicinal virtues. It has aphrodisiac, carminative, digestive, diuretic, emmenagogic, stimulating, and tonic properties. In Ayurveda, it is used as another type, the *Cyperus rotundus*, for the treatment of flatulence, indigestion, diarrhea, dysentery, and excessive thirst. In Morocco in particular, the rushnut was regarded in the past as having spermatogenic, aphrodisiac and galactogenic powers.

The purpose of this invention is the use of an active ingredient that is obtained from *Cyperus esculentus* in or for the preparation of a cosmetic and/or dermopharmaceutical composition that is designed to combat cutaneous aging. Preferably, said active ingredient is able to work on the papillary dermis, in particular:

By limiting the degradation of oxytalan fibers and by stimulating the synthesis of fibrillin-1, primary component of papillary fibroblasts, so as to restore the functional organization of the micofibrillar network of oxytalan of the papillary dermis, and/or By stimulating the expression of specific functional collagens XVI of the papillary dermis, and thus to improve the flexibility of the skin, and/or By stimulating the expression of specific functional collagens XII of the papillary dermis and thus to improve the deformability of the skin, and/or By stimulating the expression of the matrix collagens I, so as to improve the matrix architecture and the resistance of the skin, and/or By stimulating the expression of the matrix collagens VI and to improve the cohesion and the flexibility of the skin.

Advantageously, according to the invention, the use of at least one active ingredient that is obtained from *Cyperus esculentus* makes it possible to combat the appearance of wrinkles, to reduce the fatigability of the skin linked to the cutaneous aging, and/or to increase its elasticity and/or its deformability.

The active ingredient that is obtained from *Cyperus esculentus* according to the invention is designed to be incorporated within cosmetic and/or dermopharmaceutical compositions.

The composition according to the invention can contain 0.01 to 20% of at least one active ingredient that is obtained from *Cyperus esculentus*.

The administration of a cosmetic and/or dermopharmaceutical composition that contains at least one active ingredient that is obtained from *Cyperus esculentus* according to the invention is preferably done topically.

The composition according to the invention can come in the form of creams, oil-in-water emulsions, water-in-oil or multiple emulsions, solutions, suspensions, or else powders. Preferably, it comes in the form of a gel, a solution or an emulsion, and it comprises:

Between 0.01% and 20% of at least one active ingredient that is obtained from Cyperus esculentus, as an anti-aging agent, At least one additional ingredient, selected from among the additional raw materials that are used in cosmetics, preferably glycerol, and A dermatologically acceptable vehicle.

According to another aspect, the object of the invention is a particular active ingredient that is obtained from *Cyperus esculentus* and is designed to combat cutaneous aging and is able to work on the synthesis of at least one fibrous molecule of the papillary dermis. This active ingredient is able to be obtained by a process that comprises the following stages:

Solubilization of *Cyperus esculentus* tuber powder in water,

Successive enzymatic hydrolyses,

Separation of soluble and insoluble phases, and

Enzymatic inactivation by heat treatment.

The invention also covers a process for the production of this active ingredient.

This invention is now described in detail by using an example of an active ingredient that is obtained from *Cyperus esculentus* and test results.

1. PROCESS FOR THE PRODUCTION OF AN ACTIVE INGREDIENT ACCORDING TO THE INVENTION

The active ingredient that is obtained from *Cyperus esculentus* and that is useful according to the invention is able to be produced by a process that comprises the following stages:

Solubilization of *Cyperus esculentus* tuber powder in water,

Successive enzymatic hydrolyses,

Separation of soluble and insoluble phases, and

Enzymatic inactivation by heat treatment.

The enzymes that are used are carbohydrases. These can be purified enzymes, single-component enzymes, or else a mixture of different enzymes. By way of example, it is possible to cite starch degraded by alpha-amylase, beta-1,4 amylase, glucosamylase; hemicellulases such as arabinase, arabinofuranosidase, xynalase, 1,3- or 1,4-beta-xylosidase, beta-1,4-galactanase, alpha-galactosidase, beta-galactosidase, mannase; cellulases such as cellobiohydrolase, endoglucanase; pectinases such as rhamnogalacturonase, rhamnopyranohydrolase, polygalacturonase, glucuronisidase; or else beta-glucanase or beta-glucosidase.

The enzymatic inactivation can be followed by one or more stages of filtration and/or concentration. Preferably, enzymatic inactivation is followed by the following stages:

Filtration

Purification of the active fraction by ultrafiltration, and

Filtration and sterilizing filtration.

The active ingredient can be obtained in liquid form or in powder form by atomization or freeze-drying.

2. CHARACTERIZATION OF AN ACTIVE INGREDIENT ACCORDING TO THE INVENTION

According to a second aspect, the invention relates to an anti-aging cosmetic active ingredient, obtained from *Cyperus esculentus* and able to be produced by the implementation of the process presented above.

Preferably, the active ingredient is obtained from *Cyperus esculentus* tuber powder.

Preferably, the active ingredient according to the invention is in liquid form.

It can be defined by the characteristics that are disclosed below.

2-1. Dry Materials:

The level of dry materials is measured by running a sample with a given initial weight through the oven at 105° C. in the presence of sand until a constant weight is obtained.

The level of dry materials of an active ingredient that is obtained from Cyperus esculentus according to the invention is between 10 and 250 g/l, more particularly between 38 and 52 g/l.

2-2. Measurement of the pH:

The pH that is measured by the potentiometric method at ambient temperature leads to values of between 3 and 7, more particularly between 4.5 and 5.5.

2-3. Determination of the Total Sugar Content:

The DUBOIS method is used. In the presence of concentrated sulfuric acid and phenol, the reducing sugars provide an orange-yellow compound. Starting from a standard range, it is possible to determine the total sugar level of a sample.

The total sugar level of an active ingredient that is obtained from *Cyperus esculentus* according to the invention is between 8 and 240 g/l, preferably between 32 and 50 g/l.

2-4. Characterization of Monomeric Sugars:

The characterization of monomeric sugars of an active ingredient that is obtained from *Cyperus esculentus* according to the invention is conducted by high-performance liquid chromatography (HPLC).

The results that are obtained show that an active ingredient that is obtained from *Cyperus esculentus* according to the invention consists, in decreasing order, of glucose, galactose, arabinose, xylose, mannose and rhamnose. In particular, its glucidic fraction comprises at least 95% glucose.

2-5. Characterization of Carbohydrates:

The determination of the size of the carbohydrates of an active ingredient that is obtained from *Cyperus esculentus* according to the invention is done by high-performance liquid chromatography.

The chromatogram that is obtained shows the presence of more than 90% monosaccharides with a molecular weight that is less than 180 Da and less than 10% oligosaccharides with a molecular weight of between 300 and 2,500 Da. The glucidic fraction of the active ingredient that is obtained from *Cyperus esculentus* according to the invention therefore consists essentially of glucose that is present in the form of monosaccharides and oligosaccharides.

2-6. Identification of the Active Fraction:

The active fraction of the active ingredient that is obtained from *Cyperus esculentus*, working on the expression of the mRNA (messenger ribonucleic acid) that codes for collagen I, consists for the most part of oligosaccharides with a molecular weight that is more than 900 Da.

3. EVALUATION OF THE EFFECT OF AN ACTIVE INGREDIENT THAT IS OBTAINED FROM *CYPERUS ESCULENTUS* ACCORDING TO THE INVENTION

The extract that is used for the following studies is an extract of *Cyperus esculentus* that is obtained by the implementation of a process that comprises the following stages:

Solubilization of *Cyperus esculentus* tuber powder in water at a rate of 50 g/l, Successive enzymatic hydrolyses by means of two carbohydrases, Separation of soluble and insoluble phases by decanting during one night, Enzymatic inactivation by heat treatment at 90° C. for 3 hours, Purification of the active fraction by ultrafiltration, and Sterilizing filtration on a filter of 0.22 µm.

The active ingredient that is obtained has the following characteristics:

Appearance: Clear liquid

Color: Clear amber

Dry materials: 50.1 g/l

Total sugars: 36.2 g/l in the form of monosaccharides and oligosaccharides,

Total proteins: 6.0 g/l (the total protein level is obtained by the Kjedhal method—*Official Method of Analysis of the A.O.C.* 1975, 12$^{th}$ ed. W. Horwitz, E.D., New York, pp. 15-60)

Ashes: 7.8 g/l (the content of raw ashes is determined by the weighing of residues obtained from incineration at 550° C. in an electric muffle furnace)

Polyphenols=0.1 g/l (the metering of the phenolic compounds is achieved using potassium ferricyanide by referring to a standard range of gallic acid of 40 to 120 mg/l).

This extract example is, of course, not limiting.

3.1 Evaluation of the In-Vitro Effect

The protocol that is used to install the cellular models of the following studies refers to the publication "J. M. SORELL et al., *Journal of Cellular Physiology*, 200: 134-145 (2004)."

3.1.1. —Effect of an Active Ingredient that is Obtained from *Cyperus Esculentus* on the Synthesis of the Microfibrillar Network of Oxytalan a—Quantification on Normal and Senescent Papillary Fibroblasts by Western Blot The objective of this study is to evaluate the effect of an active ingredient that is obtained from *Cyperus esculentus* according to the invention on the synthesis of the microfibrillar network of oxytalan by using fibrillin-1, the major component of these fibers, as a marker.

The study is done by Western Blot on normal and senescent papillary human fibroblasts whose aging is induced by successive runs.

The operating protocol is as follows.

On day 1, the fibroblasts are inoculated in the complete medium MEM, and then incubated at 37° C.

On day 2, the cells are treated. For the normal papillary fibroblasts and for the senescent papillary fibroblasts, the culture medium is eliminated and replaced by the medium MEM that may or may not contain an active ingredient that is obtained from *Cyperus esculentus* according to the invention at 0.5% and 1%.

The cells are then incubated at 37° C.

On day 4, the cellular supernatants are recovered and concentrated, and then stored at −80° C.

A Western Blot is then produced to meter the fibrillin-1.

The results that are obtained are presented in the table below:

|  | Synthesis of Fibrillin-1 (%) | |
| --- | --- | --- |
|  | Normal Papillary Fibroblasts | Aged Papillary Fibroblasts |
| Untreated Control | 100 | 69 |
| Active Ingredient that is Obtained from 0.5% *Cyperus esculentus* | 116 | 105 |
| Active Ingredient that is Obtained from 1% *Cyperus esculentus* | 123 | 113 |

The synthesis of fibrillin-1 by the senescent papillary fibroblasts is significantly reduced by 31% relative to the normal control papillary fibroblasts.

It is noted that tested at 1%, the active ingredient that is obtained from *Cyperus esculentus* according to the invention increases the synthesis of fibrillin-1 by normal papillary fibroblasts of 23% and significantly restores the synthesis of fibrillin-1 by the senescent papillary fibroblasts at a rate that is similar to that of the normal control papillary fibroblasts.

b—Display of Human Skin Explants by Histological Coloring

The objective of this study is to evaluate the effect of an active ingredient that is obtained from *Cyperus esculentus* according to the invention on the synthesis of oxytalan fibers, specific network of the papillary dermis.

The study is done on human skin explants that are obtained from a young donor and an aged donor. The display is obtained according to histological coloring.

In a first step, the operating protocol consists in treating the skin explants and then in producing the coloring of the oxytalan fibers.

On day 1, punches 8 mm in diameter are produced from human plastic surgery and maintained within the culture medium.

From day 2 to day 8, these explants are treated topically with a placebo or active ingredient according to the invention that is formulated at 4% once per day for 7 days.

On day 9, the explants are recovered and frozen. Slices are then made.

The coloring of the oxytalan fibers on the slices according to the protocol described by "Ph.D. G. GODEAU et al. *Analytical and Quantitative Cytology and Histology*, 8, 4: 321-325 (1986)" is then done.

The coloring is then displayed using a microscope coupled to an image analysis system. The oxytalan fibers appear specifically in dark blue and are perpendicular to the basal membrane.

The histological results being qualitative, three levels of expression have been defined:

Low detection of coloring +
Average detection of coloring ++
High detection of coloring +++

The results that are obtained are presented in the following table:

|  | Synthesis of Oxytalan Fibers |
|---|---|
| 28-Year-old Explant Treated with Placebo | +++ |
| 55-Year-old Explant Treated with Placebo | + |
| 55-Year-old Explant Treated with the 4% Active Ingredient According to the Invention | ++ |

On a skin explant of an aged donor, the number of oxytalan fibers is reduced, and the organization of the fibers perpendicular to the DEJ is greatly altered in comparison to the young donor explant.

These results show that tested ex-vivo at 4% on an aged donor explant, an active ingredient that is obtained from *Cyperus esculentus* according to the invention makes it possible to reboost the synthesis of the microfibrillar network of oxytalan and to restore its functional organization.

3.1.2—Effect on the Expression of Collagens

The objective of this study is to evaluate the effect of an active ingredient that is obtained from *Cyperus esculentus* according to the invention on its capacity to increase the expression of the mRNA that codes for the collagens XVI, XII, VI and I.

This study is done by quantitative PCR on normal and senescent papillary human fibroblasts according to the operating protocol that is described below.

On day 1, the normal or senescent human papillary fibroblasts are inoculated and then incubated at 37° C.

On day 3, the cells are treated with an active ingredient that is obtained from *Cyperus esculentus* according to the invention at 0.5% or 1% or with a reference molecule, TGFFβ-1 at 1 ng/ml. They are then incubated at 37° C.

On day 5, the cells are recovered, and the total amount of RNA is extracted. The RNAs are reverse transcripts, and the complementary DNAs (deoxyribonucleic acids) that are obtained are analyzed by quantitative PCR.

The results that are obtained are presented in the following tables:

| | Level of Collagen XVI (%) | |
|---|---|---|
| | Normal Papillary Fibroblasts | Senescent Papillary Fibroblasts |
| Untreated Control | 100 | 31 |
| TGFβ-1 at 1 ng/ml | 172 | 156 |
| Active Ingredient Obtained from 0.5% *Cyperus esculentus* | 101 | 114 |
| Active Ingredient Obtained from 1% *Cyperus esculentus* | 109 | 131 |

| | Level of Collagen XII (%) | |
|---|---|---|
| | Normal Papillary Fibroblasts | Senescent Papillary Fibroblasts |
| Untreated Control | 100 | 10 |
| TGFβ-1 at 1 ng/ml | 135 | 66 |
| Active Ingredient Obtained from 0.5% *Cyperus esculentus* | 96 | 35 |
| Active Ingredient Obtained from 1% *Cyperus esculentus* | 99 | 60 |

| | Level of Collagen VI (%) | |
|---|---|---|
| | Normal Papillary Fibroblasts | Senescent Papillary Fibroblasts |
| Untreated Control | 100 | 22 |
| TGFβ-1 at 1 ng/ml | 156 | 143 |
| Active Ingredient Obtained from 0.5% *Cyperus esculentus* | 95 | 130 |
| Active Ingredient Obtained from 1% *Cyperus esculentus* | 98 | 162 |

| | Level of Collagen I (%) | |
|---|---|---|
| | Normal Papillary Fibroblasts | Senescent Papillary Fibroblasts |
| Untreated Control | 100 | 17 |
| TGFβ-1 at 1 ng/ml | 212 | 213 |
| Active Ingredient Obtained from 0.5% *Cyperus esculentus* | 97 | 55 |
| Active Ingredient Obtained from 1% *Cyperus esculentus* | 98 | 77 |

It is noted that the expression of mRNA of the collagens XVI, XII, VI and I by the senescent human papillary fibroblasts are reduced by 69%, 90%, 78%, and 83% respectively, relative to the normal human papillary fibroblasts.

The results that are obtained show that an active ingredient that is obtained from *Cyperus esculentus* according to the invention that is metered at 1% restores the expression of the mRNA of the collagens XVI and VI and tends to restore that of the collagens XII and I to a level that is similar to that of the normal control papillary fibroblasts.

3.2 Evaluation of the In-Vivo Effect 3.2.1. —Effect on Cutaneous Resiliency

This study has the objective of evaluating in vivo the effectiveness of an active ingredient that is obtained from *Cyperus esculentus* according to the invention and that is formulated with 4% in emulsion vs. placebo on the resiliency of the skin.

This study is conducted on 20 healthy female volunteers who are between 45 and 73 years old.

The measurements are made at the bottom of the face using a cutometer: the skin is aspirated by a constant-underpressure probe for a constant period. The depth of penetration of the skin in the probe is measured by two optical prisms, which makes it possible to obtain curves from which it is possible to calculate various characteristic parameters of the mechanical properties of the skin. Among these parameters, this study consists in observing the following parameters:

R4, which represents the fatigability of the skin (if R4 decreases, the "skin fatigue" effect is less significant), R5, which represents the elasticity of the skin (if R5 increases, the elasticity of the skin increases), R8, which represents the capacity of the skin to return to its initial state (if R8 increases, the capacity of the skin to return to its initial state increases).

The protocol of the study is disclosed below.

Between day −15 and day 0, the volunteers apply a placebo cream twice daily.

On day 0, two symmetrical cutaneous zones are determined at the bottom of the face, and the biomechanical properties of the skin are measured in these two zones.

Between day 0 and day 27, the volunteers apply—twice daily—the placebo and the product that contains the active ingredient that is obtained from *Cyperus esculentus* according to the invention.

On day 28, measurements of the biomechanical properties of the skin on the two zones of the face that are being studied are made.

Between day 28 and day 55, the volunteers apply—twice daily—the placebo and the product that contains the active ingredient that is obtained from *Cyperus esculentus* according to the invention.

On day 56, measurements of the biomechanical properties of the skin on the two zones of the face that are being studied are made.

The results that are obtained are presented in the table below:

|  | Variation Relative to the Placebo (%) | |
| --- | --- | --- |
|  | Day 28 | Day 56 |
| R4 | −11% | −13% |
| R5 | +5% | +15% |
| R8 | +7% | +10% |

The active ingredient that is obtained from *Cyperus esculentus* according to the invention makes it possible to increase the elasticity of the skin by 15% and the capacity of the skin to return to its initial state by 10%.

In addition, it is noted that twice-daily applications of the active ingredient that is obtained from *Cyperus esculentus* according to the invention for 56 days make it possible to reduce the fatigue of the skin by 13% relative to the placebo.

3.2.2—Study of Anti-Wrinkle Properties

The object of the study is to evaluate in vivo the anti-wrinkle effectiveness of an active ingredient that is obtained from Cyperus esculentus according to the invention and that is formulated with 4% emulsion vs. placebo at the crow's-feet.

The study is conducted on 20 female volunteers of between 45 and 73 years of age.

The anti-wrinkle effectiveness is measured by means of silicone imprints made in the crow's-feet of volunteers. The analysis of these imprints using a profilometer equipped with an image analyzer makes it possible to obtain three parameters: the number of wrinkles, the total wrinkled surface, and the total length of the wrinkles.

The study is conducted according to the protocol below.

Between day −15 and day 0, the volunteers apply a placebo cream twice daily.

On day 0, two symmetrical cutaneous zones are determined at the crow's-feet, one designed to be treated by the placebo, and the other by the formulated active ingredient, and imprints are taken of these two zones.

Between day 0 and day 27, the active ingredient and the placebo are applied twice daily.

On day 28, imprints are taken of the two zones that are being studied.

Between day 28 and day 55, the formulated active ingredient and the placebo are applied twice daily.

On day 56, imprints are taken of the two zones that are being studied.

The results that are obtained for the active ingredient relative to those obtained for the placebo are expressed in percentage in the following table:

|  | Variation/Placebo (%) | |
| --- | --- | --- |
|  | Day 28 | Day 56 |
| Number of Wrinkles | −21 | −25 |
| Total Wrinkled Surface | −26 | −40 |
| Total Length | −19 | −30 |

It is noted that after 28 days of twice-daily applications in comparison to the placebo, the active ingredient that is obtained from *Cyperus esculentus* according to the invention that is formulated with 4% emulsion simultaneously reduces the number of wrinkles by 21%, the total wrinkled surface by 26%, and the total length of the wrinkles by 19%. After 56 days, the reduction is by 25% for the number of wrinkles, by 40% for the total wrinkled surface, and by 30% for the total length of the wrinkles

4. EXAMPLES OF COMPOSITION

This invention also covers the cosmetic and/or dermopharmaceutical compositions that include at least one active ingredient that is obtained from *Cyperus esculentus* according to this invention in different galenical shapes, adapted to the administration by cutaneous topical means.

These compositions can come in particular in the form of creams, oil-in-water emulsions, water-in-oil emulsions, multiple emulsions, solutions, suspensions or powders. They can be more or less fluid and may have the appearance of a cream, a lotion, a milk, a serum, an ointment, a gel, a paste or a foam, or a solid form.

These compositions contain between 0.01 and 20% by weight of active ingredient(s) obtained from *Cyperus esculentus* according to this invention.

It is possible to cite formulations that have shown a physical stability including 5% active ingredient according to the invention.

Clear Gel:
  Carbopol: 0.5% with triethanolamine: sufficient quantity for pH=6.5
  Glycerol: 10%
  Propylene glycol: 10%
  Preservative: 1.0%
  Active ingredient: 5.0%
  Water: 73.5%

Opaque Gel:
  Sepigel 305: 3%
  Lanol 99: 12%
  Preservative: 1.0%
  Active ingredient: 5.0%
  Water: 79%

Emulsified Gel:
  Montanov 202: 3.0%
  Isopropyl palmitate: 10%
  Preservative: 1.0%
  Sepigel 305: 2%
  Active ingredient: 5.0%
  Water: 79%

Non-ionic Emulsion:
  Montane 60: 2.0%
  Montanox 60: 4.0%
  Isopropyl myristat: 8%
  Paraffin wax 130/135: 3%
  Preservative: 1.0%
  Active ingredient: 5.0%
  Water: 77%

Anionic Emulsion:
  Stearic acid: 7.0% triethanolamine, sufficient quantity for pH=8
  Ritaphyl ICS: 20%
  Preservative: 1.0%
  Active ingredient: 5.0%
  Water: 67%

Cationic Emulsion:
  Quaternium-82: 5.0%
  Cetyl alcohol: 1%
  Gemseal 60: 8%
  Cetearyl alcohol: 1%
  PEG-100 stearate: 1%
  Preservative: 1.0%
  Active ingredient: 5.0%
  Water: 78%

In addition, tests have shown the compatibility of the active ingredient with the raw materials used in cosmetics: thickeners, emulsifiers, and solvents.

It is also possible to cite examples of anti-aging cosmetic compositions including the active ingredient according to the invention. The composition examples that follow are obtained by mixing different components. The amounts that are indicated are provided by percentage of weight.

4.1 Example of an Eye Outline Serum
  The formulation is as follows:

| | |
|---|---|
| Simulgel EG (Seppic): | 2% |
| DUB 1632 (Stearinerie Dubois): | 1% |
| DC 345 (Dow Corning): | 2% |
| Ritox 59 (Rita): | 1% |
| Glycerox 767 HC (Croda): | 4% |
| DUB MCT 5545 (Stearinerie Dubois) | 2% |
| Preservative: | 1% |
| Active ingredient according to the invention: | 4% |
| Water: sufficient quantity for | 100% |

4.2 Example of a Silicone-Containing Face Cream
  The formulation is as follows:

| | |
|---|---|
| Glycerin: | 3% |
| Butylene glycol: | 2% |
| Propylene glycol: | 2% |
| Phytosqualane (Sophim): | 8% |
| DUB STG 30 AE (Stearinerie Dubois): | 4% |
| DC 345 (Dow Corning): | 25% |
| Parma oil (Sictia): | 4% |
| DUB heliocrystal (Stearinerie Dubois): | 4% |
| Preservative: | 1% |
| Active ingredient according to the invention: | 4% |
| Water: sufficient quantity for | 100% |

4.3 Example of a Night Cream
  The formulation is as follows:

| | |
|---|---|
| Emulgade 1000 NI (Henkel): | 1% |
| Montane 60 (Seppic): | 1% |
| Rita CA (Rita): | 1% |
| Ritacane (Rita): | 4% |
| Sophim MC 30 (Sophim): | 6% |
| Sucrose ester SP30 C (Sisterna): | 1% |
| Preservative: | 1% |
| Active ingredient according to the invention: | 4% |
| Water: sufficient quantity for | 100% |

4.4 Example of a Lactescent Hydrating Gel
  The formulation is as follows:

| | |
|---|---|
| Ultrez 21 (Noveon): | 0.2% |
| Glycerin: | 9% |
| EDT 2020 (Noveon): | 0.27% |
| Blanose 9M31F (Hercules): | 0.2% |
| DUB Synersol (Stearinerie Dubois): | 6% |
| Montanox 80 (Seppic): | 3% |
| NaOH: sufficient quantity for | pH = 6.2 |
| Preservative: | 1% |
| Active ingredient according to the invention: | 4% |
| Water: sufficient quantity for | 100% |

The invention claimed is:

1. A method for treating cutaneous aging in a subject in need thereof, consisting essentially of:
  administering to the subject's skin a composition consisting essentially of 0.01-20% of a *Cyperus esculentus* extract;
  wherein said extract has:
  a dry materials content of between 10 and 250 g/l,
  a pH between 3 and 7, and
  a total sugar content of between 8 and 240 g/l; and
  wherein said extract is able to:
  work on the synthesis of at least one specific fibrous molecule of the papillary dermis,
  increase the expression of functional collagens XII and/or XVI and/or oxytalan fibers and/or fibrillin-1 fibers of the papillary dermis, and
  increase the expression of matrix collagens I and/or VI.

* * * * *